(12) United States Patent
Couturier et al.

(10) Patent No.: US 7,772,340 B2
(45) Date of Patent: *Aug. 10, 2010

(54) ALKOXYAMINES ORIGINATING FROM β-PHOSHORATED NITROXIDES AND USE THEREOF IN RADICAL POLYMERISATION

(75) Inventors: Jean-Luc Couturier, Lyons (FR); Olivier Guerret, La Tour de Salvigny (FR); Denis Bertin, Marseilles (FR); Didier Gigmes, Marseilles (FR); Sylvain Marque, Antraigues sur Volane (FR); Paul Tordo, Marseilles (FR); Florence Chauvin, King of Prussia, PA (US); Pierre-Emmanuel Dufils, Saint Aubin Epinay (FR)

(73) Assignee: Arkema France, Colombes (FR)

( * ) Notice: Subject to any disclaimer, the term of this patent is extended or adjusted under 35 U.S.C. 154(b) by 998 days.

This patent is subject to a terminal disclaimer.

(21) Appl. No.: 10/523,481

(22) PCT Filed: Jul. 23, 2003

(86) PCT No.: PCT/FR03/02328

§ 371 (c)(1),
(2), (4) Date: Jan. 31, 2006

(87) PCT Pub. No.: WO2004/014926

PCT Pub. Date: Feb. 19, 2004

(65) Prior Publication Data

US 2006/0142511 A1 Jun. 29, 2006

(30) Foreign Application Priority Data

Aug. 7, 2002 (FR) .................................. 02 10030
May 2, 2003 (FR) .................................. 03 03169

(51) Int. Cl.
*B01J 27/24* (2006.01)
*C08F 2/32* (2006.01)
*C08F 118/02* (2006.01)
*C07F 9/40* (2006.01)

(52) U.S. Cl. .................. 526/217; 526/193; 526/213; 526/215; 526/216; 526/220; 526/236; 526/303.1; 526/307.6; 526/317.1; 526/318.3; 526/318.4; 526/319; 526/326; 526/328; 526/329.7; 528/399; 528/422; 558/153; 558/166; 558/169; 558/175; 560/130; 560/170; 560/155; 560/179; 564/15; 564/300; 564/301; 564/305; 568/8

(58) Field of Classification Search ................ 526/193, 526/217, 220, 236, 319, 328, 329.7; 558/153, 558/166, 169, 175; 560/170; 564/15
See application file for complete search history.

(56) References Cited

U.S. PATENT DOCUMENTS 5,763,548 A * 6/1998 Matyjaszewski et al. .... 526/135

| | | | |
|---|---|---|---|
| 6,353,065 B1 * | 3/2002 | Charleux et al. ............ 526/220 |
| 6,495,720 B1 | 12/2002 | Couturier et al. |
| 6,569,967 B1 * | 5/2003 | Couturier et al. ............ 526/193 |
| 6,624,322 B1 | 9/2003 | Gillet et al. |
| 6,657,043 B1 | 12/2003 | LeMercier et al. |
| 7,199,214 B2 * | 4/2007 | Couturier et al. ............ 528/422 |
| 7,214,810 B2 * | 5/2007 | Couturier et al. ............ 558/87 |
| 2003/0149205 A1 * | 8/2003 | Callais et al. ............... 526/220 |
| 2005/0215691 A1 * | 9/2005 | Muhlebach et al. ......... 524/445 |
| 2007/0167591 A1 * | 7/2007 | Couturier et al. ............ 526/278 |
| 2008/0221354 A1 * | 9/2008 | Couturier et al. ............ 564/15 |

OTHER PUBLICATIONS

Le Mercier, Christophe; Acerbis, Sebastien; Bertin, Denis; Chauvin, Florence; Gigmes, Didier; Guerret, Olivier; Lansalot, Muriel; Marque, Sylvain; Le Moigne, Francois; Fischer, Hanns; Tordo, Paul. "Design and use of β-phosphorus nitroxides and alkoxyamines in controlled/"living" free radical polymerizations". Macromol. Symp. 2002, 182, 225-247.*

Ananchenko, Gennady; Matyjaszewski, Krzysztof. "Controlled/Living Radical Polymerization of tert-Butyl Acrylate Mediated by Chiral Nitroxides. A Stereochemical Study". Macromolecules (2002), 35(22), 8323-8329.*

(Continued)

*Primary Examiner*—Vasu Jagannathan
*Assistant Examiner*—Richard A Huhn
(74) *Attorney, Agent, or Firm*—Steven D. Boyd (57) ABSTRACT

A subject-matter of the invention is alkoxyamines resulting from β-phosphorated nitroxides corresponding to the formula:

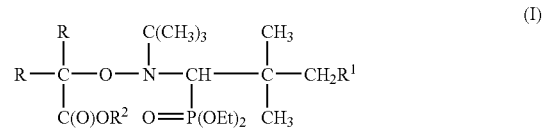

in which R represents an alkyl radical having a number of carbon atoms ranging from 1 to 3, $R^1$ represents a hydrogen atom or a residue:

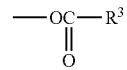

in which $R^3$ represents an alkyl radical having a number of carbon atoms ranging from 1 to 20, and $R^2$ represents a hydrogen atom, an alkyl radical having a number of carbon atoms ranging from 1 to 8, a phenyl radical, an alkali metal, such as Li, Na or K, $H_4N^+$, $Bu_4N^+$ or $Bu_3HN^+$, exhibiting a kinetic dissociation constant kd, measured at 120° C. by EPR, of greater than 0.05 $s^{-1}$. These compounds can be used as initiators for the (co)polymerizations of at least one monomer which can be polymerized by the radical route.

8 Claims, 7 Drawing Sheets

OTHER PUBLICATIONS

Ashford, E. J. et al., "First example of the atom transfer radical polymerisation of an acidic monomer: direct synthesis of methacrylic acid copolymers in aqueous media", Chem. Commun. 1999, 1285-1286.*

J. American Chem. Soc.; D. Benoit et al; 121; pp. 3904-3920; 1999.

Macromulecules; S. Marque et al; 33; pp. 4403-4410; 2000.

* cited by examiner

ALKOXYAMINES ORIGINATING FROM β-PHOSHORATED NITROXIDES AND USE THEREOF IN RADICAL POLYMERISATION

TECHNICAL FIELD

A subject-matter of the present invention is α,β,β-trisubstituted hydroxylamines, hereafter denoted by alkoxylamines, obtained in particular from β-phosphorated nitroxides, which can be used as initiators for radical polymerizations.

PRIOR ART

FR 2 789 991 A1 discloses alkoxyamines resulting from β-phosphorated nitroxides, such as N-(tert-butyl)-N-(1-diethoxyphosphoryl-2,2-dimethylpropyl)-0-(1-methyl-1-(methoxycarbonyl)ethyl)hydroxylamine, which, used as initiators for polymerizations or copolymerizations of at least one monomer which can be polymerized by the radical route, provide excellent control of the polydispersity while ensuring a good rate of polymerization or of copolymerization.

However, the Applicant Company has found that there were some disadvantages to the use of the said alkoxyamines in the polymerization or the copolymerization of certain monomers which can be polymerized by the radical route.

Thus, it is difficult to achieve high molar masses. In addition, risks of runaway of the polymerization are observed with monomers having high propagation constants (kp), such as certain acrylates, when these initiators are used alone.

Without the Applicant Company being committed to any one explanation, it believes that, at the very start of the initiation of the polymerization of monomers having high kp values, in the presence of the said alkoxyamines, there is production of R• hydrocarbonaceous radicals which propagate very quickly to result in very high masses. This initial propagation reaction is very exothermic and runaway of the radical polymerization occurs. The persistant nitroxide radical >NO•, formed from the homolytic cleavage of an alkoxyamine >N—O—A according to the reaction scheme:

with an excessively low kinetic dissociation constant kd with respect to kp, can no longer control the polymerization reaction as it is found to be in an insufficient concentration to control the growth of the chains and thus the evolution of heat.

In order to overcome this disadvantage, some authors have added, at the beginning of polymerization, in addition to the alkoxyamine, a nitroxide (D. Benoit et al., J. Am. Chem. Soc., 121, pages 3904-3920,1999).

It is unsatisfactory to proceed in this way industrially as the alkoxyamine/nitroxide ratio has to be constantly adjusted to the type of monomer or mixture of monomers to be polymerized and to the polymerization temperature.

Furthermore, it is very difficult, when using the said alkoxyamines, to control the polymerization of alkyl methacrylates, such as methyl methacrylate (MMA), or the copolymerization of mixtures of monomers comprising high proportions of alkyl methacrylates.

ACCOUNT OF THE INVENTION

The Applicant Company has now found that the use of certain alkoxyamines derived in particular from β-phosphorated nitroxides as intiators for polymerizations or copolymerizations of at least one monomer which can be polymerized by the radical route makes it possible to overcome the abovementioned disadvantages.

A subject-matter of the invention is thus the use of alkoxyamines of formula:

in which R represents a linear or branched alkyl radical having a number of carbon atoms ranging from 1 to 3, $R^1$ represents a hydrogen atom or a residue:

in which $R^3$ represents a linear or branched alkyl radical having a number of carbon atoms ranging from 1 to 20, and $R^2$ represents a hydrogen atom, a linear or branched alkyl radical having a number of carbon atoms ranging from 1 to 8, a phenyl radical, an alkali metal, such as Li, Na or K, $H_4N^+$, $Bu_4N^+$ or $Bu_3HN^+$, exhibiting a kinetic dissociation constant kd, measured at 120° C. by EPR, of greater than 0.05 s$^{-1}$ and preferably of greater than 0.1 s$^{-1}$.

It is preferable, among the alkoxyamines of formula (I), to use very particularly those in which R=$CH_3$—, $R^1$=H and $R^2$=H, $CH_3$—, $(CH_3)_3C$—, Li and Na.

The alkoxyamines of formula (I) in which $R^1$=H and $R^2$ represents a linear or branched alkyl radical having a number of carbon atoms ranging from 1 to 6 are known.

Another subject-matter of the invention is thus the alkoxyamines of formula (I), with the exception of the alkoxyamines of formula (I) in which $R^1$=H and $R^2$ represents a linear or branched alkyl radical having a number of carbon atoms ranging from 1 to 6.

The alkoxyamines of formula (I) can be prepared according to methods known in the literature. The commonest method involves the coupling of a carbonaceous radical with a nitroxide radical.

Use will preferably be made, among all these methods, for the preparation of the compounds of formula (I), of the method involving the ATRA (Atom Transfer Radical Addition) reaction, as disclosed in FR 2 791 979 A1 incorporated in the present document by reference.

This method consists in reacting a nitroxide of formula:

with a halogenated derivative of formula:

(III)

in which X represents a chlorine atom or a bromine atom, R, $R^1$ and $R^2$ having the same meanings as in the formula (I), in a water-immiscible organic solvent medium in the presence of an organometallic system $MA(L)_n$ (IV) in which:
M represents a metal, such as Cu, Ag and/or Au and preferably Cu,
A represents a chlorine atom or a bromine atom,
L represents a ligand of the metal M and is chosen from polyamines, such as:
tris[2-(dimethylamino)ethyl]amine:

N,N,N',N',N''-pentamethyldiethylenetriamine (PMDETA):

N,N,N',N'-tetramethylethylenediamine:

1,1,4,7,10,10-hexamethyltriethylenetetramine (HMTETA):

cyclic polyamines, such as:
1,4,7-trimethyl-1,4,7-triazacyclononane,
1,5,9-trimethyl-1,5,9-triazacyclododecane,
1,4,8,11-tetramethyl-1,4,8,11-tetraazacyclotetradecane,
by mixing a metal salt MA, the ligand L, the halogenated derivative (III) and the nitroxide (II) according to a molar ratio (III)/(II) ranging from 1 to 1.4 with stirring in the organic solvent and by keeping the reaction medium stirred at a temperature of between 20° C. and 40° C. until the nitroxide (II) has completely disappeared, by then recovering the organic phase, which is washed with water, and by then isolating the alkoxyamine (I) by evaporation of the organic solvent under reduced pressure.

Use will preferably be made, as organic solvents, of aromatic hydrocarbons, such as benzene, toluene, xylenes, alkyl chlorides, and in particular $CH_2Cl$, and/or ethers.

The metal salt used is preferably CuBr.

It is also possible to introduce CuBr (in which the copper is in the 1 oxidation stage) and copper into the reaction medium.

The alkali metal salts of the alkoxyamines (I) ($R^2$=Li, Na, K) can be easily obtained, for example by dissolving, under cold conditions, the alkoxyamine (I) in the acid form ($R^2$=H) in the minimum amount of methanol and then adding 1.05 equivalents of alkali metal hydroxide in the minimum amount of water. The water/methanol mixture is evaporated under reduced pressure and the remaining water is removed azeotropically using cyclohexane or benzene.

The alkoxyamines of formula (I) according to the present invention can be used for the polymerization and the copolymerization of any monomer exhibiting a carbon-carbon double bond capable of polymerizing by the radical route. The polymerization or the copolymerization is carried out under the usual conditions known to a person skilled in the art taking into account the monomer or monomers under consideration, under bulk, solution, emulsion, suspension or miniemulsion conditions. The monomers under consideration can be chosen from vinylaromatic monomers, such as styrene or substituted styrenes, in particular α-methylstyrene and sodium styrenesulphonate, dienes, such as butadiene or isoprene, acrylic monomers, such as acrylic acid or its salts, alkyl, cycloalkyl or aryl acrylates, such as methyl; ethyl, butyl, ethylhexyl or phenyl acrylates, hydroxyalkyl acrylates, such as 2-hydroxyethyl acrylate, ether alkyl acrylates, such as 2-methoxyethyl acrylate, alkoxy- or aryloxypolyoxyalkylene glycol acrylates, such as methoxypolyethylene glycol acrylates, ethoxypolyethylene glycol acrylates, methoxypolypropylene glycol acrylates, methoxypolyethylene glycol-polypropylene glycol acrylates or their mixtures, aminoalkyl acrylates, such as 2-(dimethylamino)ethyl acrylate (ADAME), acrylates of amine salts, such as [2-(acryloyloxy)ethyl]trimethylammonium chloride or sulphate or [2-(acryloyloxy)ethyl]dimethylbenzylammonium chloride or sulphate, fluoroacrylates, silylated acrylates or phosphorus-comprising acrylates, such as alkylene glycol acrylate phosphates, methacrylic monomers, such as methacrylic acid or its salts, alkyl, cycloalkyl, alkenyl or aryl methacrylates, such as methyl, lauryl, cyclohexyl, allyl or phenyl methacrylate, hydroxyalkyl methacrylates, such as 2-hydroxyethyl methacrylate or 2-hydroxypropyl methacrylate, ether alkyl methacrylates, such as 2-ethoxyethyl methacrylate, alkoxy- or aryloxypolyalkylene glycol methacrylates, such as methoxypolyethylene glycol methacrylates, ethoxypolyethylene glycol methacrylates, methoxypolypropylene glycol methacrylates, methoxypolyethylene glycol-polypropylene glycol methacrylates or their mixtures, aminoalkyl methacrylates, such as 2-(dimethylamino)ethyl methacrylate (MADAME), methacrylates of amine salts, such as [2-(methacryloyloxy)ethyl]trimethylammonium chloride or sulphate or [2-(methacryloyloxy)ethyl]dimethylbenzylammonium chloride or sulphate, fluoromethacrylates, such as 2,2,2-trifluoroethyl methacrylate, silylated methacrylates, such as 3-methacryloyloxypropyltrimethylsilane, phosphorus-comprising methacrylates, such as alkylene glycol methacrylate phosphates, hydroxyethylimidazolidone methacrylate, hydroxyethylimidazolidinone methacrylate or 2-(2-oxo-1-imidazolidinyl)ethyl methacrylate, acrylonitrile, acrylamide or substituted acrylamides, 4-acryoylmorpholine, N-methylolacrylamide, acrylamidopropyltrimethylammonium chloride (APTAC), acrylamidomethylpropanesulphonic acid (AMPS) or is salts, methacrylamide or substituted methacrylamides, N-methylolmethacrylamide, methacrylamidopropyltrimethylammonium chloride (MAPTAC), itaconic acid, maleic acid or its salts, maleic anhydride, alkyl or alkoxy- or aryloxypolyalkylene glycol maleates or hemimaleates, vinylpyridine, vinylpyrrolidinone, (alkoxy)poly(alkylene glycol) vinyl ethers or divinyl ethers, such as methoxypoly(ethylene glycol) vinyl ether or poly(ethylene glycol) divinyl ether, alone or as a mixture of at least two abovementioned monomers.

The alkoxyamines (I) can be introduced into the polymerization or copolymerization medium at contents generally ranging from 0.005% to 40% by weight with respect to the monomer(s) employed and, preferably, at contents ranging from 0.01% to 10%.

Another subject-matter of the invention is therefore the functional (co)polymers obtained by a (co)polymerization process using the alkoxyamines of formula (I) as initiators.

There are numerous advantages to the use of the alkoxyamines (I) of the invention.

They make it possible to obtain high molar masses with good control and a low polydispersity index. No runaway of the polymerization is observed, in particular in the case of monomers with a high kp, such as butyl acrylate, this being the case in the absence of free nitroxide. They make possible (partial) control of the polymerization of alkyl methacrylates, such as MMA, in particular in the case of a mixture of monomers comprising at least 85% of alkyl methacrylate.

In the case where $R^2$ is a hydrogen, an alkali metal or a tert-butyl radical, they also make it possible to obtain functional (co)polymers exhibiting reactive functional groups which make it possible to carry out chemical conversions, such as grafting or coupling.

These chemical conversion processes preferably involve esterification, transesterification, amidation, transamidation and epoxide opening reactions. It would not be departing from the scope of the invention if an acid chloride were used as intermediate in the esterification or amidation reactions.

Esterification processes can in particular be advantageously used for preparing polymeric polyalkoxyamines from polymeric monoalkoxyamines according to the following where A represents a polyvalent structure and P a sequence of monomers, such as styrene and substituted styrenes, dienes, acrylic monomers, such as acrylic acid or alkyl acrylates, methacrylic monomers, such as methacrylic acid or alkyl methacrylates, acrylonitrile, acrylamide, vinylpyrrolidinone or a mixture of at least two abovementioned monomers.

Esterification and amidation processes can also be advantageously used for condensing polymers which are not obtained by radical polymerization, such as polyesters, polyamides or polyepoxides. These reactions thus make possible access to multiple block copolymer structures, such as polystyrene-polyester, polystyrene-polyamide, polystyrene-polyepoxide, polyacrylate-polyester, polyacrylate-polyamide or polyacrylate-polyepoxide.

The alkoxyamines of formula (I) of the present invention additionally exhibit the advantage of being stable solids which can be easily purified. Without the Applicant Company being committed to any one explanation, it is believed that this state results from the fact that, in the alkoxyamine of formula (I), the carbon carrying the R and $R^2$ radicals is not asymmetric, in contrast to the epoxyamines mentioned in FR 2 789 991 A1.

The examples which follow illustrate the invention.

General Comments:

The nitroxide used as reactant has the formula:

hereinafter denoted SG1.

It was obtained by oxidation of diethyl 2,2-dimethyl-1-(1,1-dimethylamino)propylphosphonate with peracetic acid according to a protocol disclosed in FR 2 788 270.

The compounds obtained in the synthetic examples are identified by C, H and N microanalysis and by $^1H$, $^{13}C$ and $^{31}P$ NMR.

The NMR spectra were recorded on a Bruker AC 400 device ($^1H$, 100 MHz; $^{31}P$, 40.53 MHz; $^{13}C$, 25.18 MHz). $^{13}C$ and $^{31}P$ NMR spectra are produced with $^1H$ decoupling.

The chemical shifts δ are given in ppm, with respect to tetramethylsilane (internal reference) for $^1H$ and $^{13}C$ and with respect to 85% $H_3PO_4$ (external reference) for $^{31}P$.

The solvents used are either $CDCl_3$ or $C_6D_6$.

The kinetic dissociation constants kd were measured at 120° C. by quantitative electron paramagnetic resonance (EPR) according to the method described by Sylvain Marque et al. in Macromolecules, 33, pages 4403 to 4410, 2000.

The principle consists in completely and rapidly trapping, as soon as it is formed, the transitory hydrocarbonaceous radical with a nitroxide, such as galvinoxyl (2,6-di(tert-butyl)-4-(3,5-di(tert-butyl)-4-oxocyclohexa-2,5-dien-1-ylidenmethyl)phenoxyl), to result in another unreactive alkoxyamine.

EXAMPLE 1

Preparation of 2-methyl-2-[N-(tert-butyl)-N-(diethoxyphosphoryl-2,2-dimethylpropyl)aminoxy] propionic acid Procedure:

500 ml of degassed toluene, 35.9 g of CuBr (250 mmol), 15.9 g of copper powder (250 mmol) and 86.7 g of N,N,N',N',N''-pentamethyldiethylenetriamine (PMDETA) (500 mmol) are introduced into a 2 l glass reactor purged with nitrogen and then a mixture comprising 500 ml of degassed toluene, 42.1 g of 2-bromo-2-methylpropionic acid (250 mmol) and 78.9 g of 84% SG1, i.e. 225 mmol, is introduced with stirring and at ambient temperature (20° C.).

The reaction medium is allowed to react at ambient temperature for 90 minutes and with stirring and is then filtered. The toluene filtrate is washed twice with 1.5 l of a saturated aqueous NH₄Cl solution.

A yellowish solid is obtained, which solid is washed with pentane to give 51 g of 2-methyl-2-[N-(tert-butyl)-N-(diethoxyphosphoryl-2,2-dimethylpropyl)aminoxy]propionic acid (60% yield).

The analytical results are given below:

molar mass, determined by mass spectrometry: 381.44 g.mol$^{-1}$ (for $C_{17}H_{36}NO_6P$)

elemental analysis (empirical formula: $C_{17}H_{36}NO_6P$):
  % calculated: C=53.53, H=9.51, N=3.67
  % found: C=53.57, H=9.28, N=3.77 melting determined on a Büchi B-540 device: 124° C.-125° C.

$^{31}$P NMR (CDCl₃): δ 27.7

$^{1}$H NMR (CDCl₃):
  δ 1.15 (singlet, 9H on carbons 15, 21 and 22),
  δ 1.24 (singlet, 9H on carbons 17, 23 and 24),
  δ 1.33-1.36 (multiplet, 6H on carbons 4 and 7),
  δ 1.61 (multiplet, 3H on carbon 18),
  δ 1.78 (multiplet, 3H on carbon 13),
  δ 3.41 (doublet, 1H on carbon 9),
  δ 3.98-4.98 (multiplet, 4H on carbons 3 and 6),
  δ 11.8 (singlet, —OH).

$^{13}$C NMR (CDCl₃):

| Carbon atom No. | δ |
|---|---|
| 3 and 6 | 60.28-63.32 |
| 9 | 69.86 |
| 12 | 63 |
| 13 | 28.51 |
| 14 | 36.04 |
| 15, 21 and 22 | 29.75 |
| 16 | 63.31 |
| 17, 23 and 24 | 28.74 |
| 18 | 24.08 |
| 19 | 176.70 | kd (120° C.)=0.2 s$^{-1}$.

EXAMPLES 1A AND 1B

Synthesis of alkyl 2-methyl-2-[N-(tert-butyl)-N-(1-diethoxyphosphoryl-2,2-dimethylpropyl)aminoxy]propionates

Procedure:

Cuprous bromide CuBr, copper Cu(0) and anhydrous benzene are placed in a round-bottomed flask equipped with a septum. The solution is subsequently deoxygenated by sparging with nitrogen for 10 minutes. N,N,N',N',N''-Pentamethyldiethylenetriamine (PMDETA) is subsequently introduced under an inert atmosphere. Sparging with nitrogen is maintained for an additional 10 minutes.

The α-brominated ester and the nitroxide SG1 are placed in anhydrous benzene in another round-bottomed flask. The solution is also degassed by sparging with nitrogen for 10 minutes. This solution is subsequently transferred into the first round-bottomed flask under an inert atmosphere. The reaction mixture, cooled using a water/ice mixture, is kept stirred magnetically for 15 min and then at ambient temperature for 45 min. The solution is subsequently filtered through celite and the precipitate is washed with ether. The filtrate is washed with ice-cold water until a colourless aqueous phase is obtained. The organic phase is dried over MgSO₄ at 0° C. and evaporated, to start with on a Rotavapor rotor evaporator and then on a 0.08 mbar reduced pressure line.

EXAMPLE 1A

Synthesis of tert-butyl 2-methyl-2-[N-(tert-butyl)-N-(1-diethoxyphosphoryl-2,2-dimethylpropyl)aminoxy]propionate Reactants: Benzene (18 ml+18 ml), CuBr: 1.47 g (10.2 mmol), Cu(0): 0.65 g (10.2 mmol), PMDETA: 4.3 ml (20.4 mmol), SG1: 2 g (6.8 mmol), tert-butyl 2-bromo-2-methylpropionate: 2.23 g (10.2 mmol). The alkoxyamine obtained is purified on a silica column using a 3/1 pentane/ethyl ether mixture as eluent. The alkoxyamine solidifies at −18° C. to give a white powder. Yield 70%.

kd (120° C.)=0.2 s$^{-1}$.

Melting: 44-46° C.

$^{31}$P NMR (CDCl₃, 121.59 MHz): δ 25.50 ppm.

$^{1}$H NMR (CDCl₃, 300 MHz): δ 1.12 ppm (s, 9H), 1.20 (s, 9H), 1.29 (m, 6H), 1.46 (s, 9H), 1.55 (s, 3H), 1.67 (s, 3H), 3.28 (d, $J_{H-P}$=27 Hz, 1 H), 3.90-4.16 (m, 2H), 4.27-4.45 (m, 2H).

$^{13}$C NMR (CDCl₃, 75.48 MHz): δ 16.27 ppm (d, $J_{C-P}$=6.8 Hz, O—CH₂—CH₃), 16.65 (d, $J_{C-P}$=5.3 Hz, O—CH₂—CH₃), 22.01 (s, CH₃—C(CH₃)—C═O), 27.93 (s, t-Bu), 28.15 (s, t-Bu), 28.77 (s, CH₃—C(CH₃)—C═O), 30.18 (d, $J_{C-P}$=4.52 Hz, CH—C—(CH₃)₃), 36.00 (d, $J_{C-P}$=6.0 Hz, CH—C—(CH₃)₃), 58.62 (d, $J_{C-P}$=7.5 Hz, O—CH₂—CH₃), 61.68 (d, $J_{C-P}$=6.0 Hz, O—CH₂—CH₃), 62.08 (s, N—C—(CH₃)₃), 69.93 (d, $J_{C-P}$=137.4 Hz, CH—P), 80.81 (s, O—C—(CH₃)₃), 84.41 (s, (CH₃)₂—C—C═O), 174.39 (s, C═O).

EXAMPLE 1B

Synthesis of methyl 2-methyl-2-[N-(tert-butyl)-N-(1-diethoxyphosphoryl-2,2-dimethylpropyl)aminoxy]propionate Reactants: identical to Example 1A, except that tert-butyl 2-bromo-2-methyl-propionate is replaced with the same molar amount of methyl 2-bromo-2-methylpropionate: (10.2 mmol).

The alkoxyamine is obtained without additional purification and solidifies at −18° C. to give a white powder.

kd (120° C.)=0.8 s$^{-1}$.

Melting: 56-58° C.

$^{31}$P, $^{13}$C and $^1$H NMR are in agreement with those mentioned in French Patent Application No. 2 789 991.

EXAMPLE 1C

Synthesis of sodium 2-methyl-2-[N-(tert-butyl)-N-(1-diethoxyphosphoryl-2,2-dimethylpropyl)aminoxy]propionate

The methylpropionic acid/SG1 alkoxyamine obtained in Example 1 is dissolved in the minimum amount of methanol. 1.05 equivalents of sodium hydroxide, dissolved in the minimum amount of water, are then added thereto. The water/methanol mixture is evaporated under reduced pressure until the sodium salt is obtained, which salt exists in the form of a white solid. Cyclohexane is added in order to remove the traces of water by distillation of the water/cyclohexane azeotrope.

Elemental analysis (empirical formula $C_{17}H_{35}NO_6PNa$)

Percentage calculated: C=50.61; H=8.74; N=3.47

Percentage found: C=49.29; H=8.97; N=3.01 kd (120° C.)=0.2 s$^{-1}$ $^{31}$P NMR ($C_6D_6$): δ 28.05

$^1$H NMR ($C_6D_6$):

δ 1.24-1.48 (unresolved peak, 24H on carbons 4, 7,15, 17, 21 and 24),

δ 1.91 (singlet, 3H on carbon 18),

δ 2.07 (singlet, 3H on carbon 13),

δ 3.43 (doublet, 1H on carbon 13),

δ 4.15-4.6 (unresolved peak, 4H on carbons 3 and 6)

$^{13}$C NMR ($C_6D_6$):

| Carbon atom No. | δ |
|---|---|
| 3 and 6 | 61.33-61.42 |
| 4 and 7 | 16.55-16.70 |
| 9 | 71.08 |
| 12 | 86.36 |
| 13 and 18 | 24-29.10 |
| 14 | 36.24 |
| 15, 21 and 22 | 30.23 |
| 16 | 62.42 |
| 17, 23 and 24 | 29.27 |
| 19 | 180.74 |

EXAMPLES 2, 3 and 4

Use of 2-methyl-2-[N-(tert-butyl)-N-(diethoxyphosphoryl-2,2-dimethylpropyl)-aminoxy]propionic acid, hereinafter methylpropionic acid/SG1, as initiator in the polymerization of butyl acrylate General Procedure:

The introduction of x g of alkoxyamine and 60 g of butyl acrylate (BA) into a 100 ml glass reactor equipped with a reflux condenser, an inert gas (N$_2$) inlet and a temperature probe was carried out. The medium was degassed by sparging with nitrogen for 20 minutes and was then placed, under magnetic stirring, in an oil bath thermostatically controlled at 120° C. Samples were withdrawn under an inert atmosphere at regular time intervals.

Proton NMR allowed us to monitor the conversion of the monomer. The determination of the average molar masses of the polymer and of their polydispersity indices was carried out by steric exclusion chromatography (SEC), by virtue of a universal calibration using polystyrene standards and the Mark-Houwink coefficients of poly(butyl acrylate) in THF. The chromatograms were recorded with Millenium 32 soft-

EXAMPLE 2

In Accordance with the Invention x=0.304 g of methylpropionic acid/SG1 alkoxyamine obtained according to Example 1,
the targeted theoretical mass $Mn_{th}$, expressed as being the ratio of the initial concentration of the monomer multiplied by the molar mass of the monomer to the initial concentration of alkoxyamine, at 100% conversion, is 75 000 g.mol$^{-1}$.

EXAMPLE 3

In Accordance with the Invention x=0.114 g of methylpropionic acid/SG1 alkoxyamine, $Mn_{th}$=200 000 g.mol$^{-1}$

EXAMPLE 4

Not in Accordance with the Invention x=0.114 g of MONAMS, plus 2 mg of SG1
MONAMS: N-(tert-butyl)-N-(1-diethoxyphosphoryl-2,2-dimethylpropyl)-O-(1-methyl-1-(methoxycarbonyl)ethyl) hydroxylamine
$Mn_{th}$ targeted with MONAMS is 200 000 g.mol$^{-1}$
The results are recorded in Tables 1 (Example 2), 2 (Example 3) and 3 (Example 4) below.
In these tables, t (s) represents the polymerization time in seconds,
Dc the degree of conversion and
PI the polydispersity index, which is the ratio Mw/Mn.

TABLE 1

Results of Example 2

| t (s) | Dc | In(1/(1 − Dc)) | Mn(th) | Mn | Mw | PI |
|---|---|---|---|---|---|---|
| 0 | 0 | 0 | | | | |
| 300 | 0.09 | 0.094 | 63 00 | 5 700 | 10 500 | 1.84 |
| 1 800 | 0.32 | 0.385 | 22 400 | 23 600 | 31 800 | 1.35 |
| 3 600 | 0.52 | 0.729 | 36 300 | 35 200 | 44 400 | 1.26 |
| 6 300 | 0.72 | 1.272 | 50 400 | 44 300 | 56 400 | 1.27 |

The results make it possible to plot the following kinetic curves associated with each example:
In(1/1-Tc) as a function of the time; Mn(th), Mn and PI as a function of the degree of conversion Dc.

DESCRIPTION OF THE FIGURES

The kinetic curves corresponding to the results of Example 2 are represented in the following figures.

TABLE 2

Results of Example 3

| t (s) | Dc | In(1/(1 − Dc)) | Mn(th) | Mn | Mw | PI |
|---|---|---|---|---|---|---|
| 0 | 0 | 0 | | | | |
| 720 | 0.05 | 0.048 | 9 400 | 35 500 | 50 500 | 1.42 |
| 1 200 | 0.11 | 0.116 | 22 000 | 47 500 | 66 300 | 1.40 |
| 2 400 | 0.25 | 0.287 | 50 000 | 74 500 | 108 900 | 1.46 |
| 3 300 | 0.53 | 0.755 | 106 000 | 86 300 | 148 700 | 1.72 |
| 6 000 | 0.62 | 0.967 | 124 000 | 89 700 | 172 000 | 1.92 |
| 8 400 | 0.79 | 1.560 | 158 000 | 96 800 | 168 100 | 1.74 |
| 9 600 | 0.80 | 1.609 | 160 000 | 110 900 | 177 200 | 1.60 |
| 12 600 | 0.82 | 1.714 | 164 000 | 141 800 | 220 700 | 1.56 |

Figure 1:
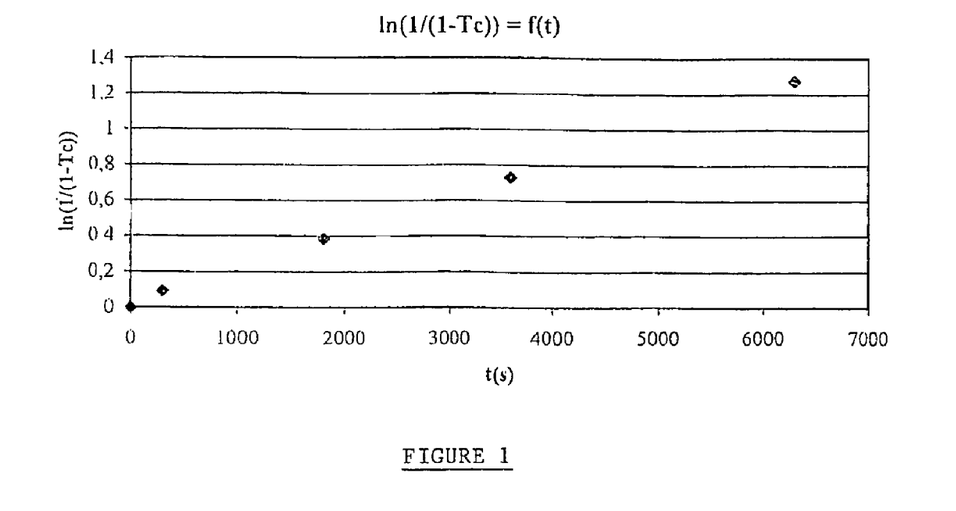
FIG. 1: In(1/(1-Dc))=f(t)
Figure 2:
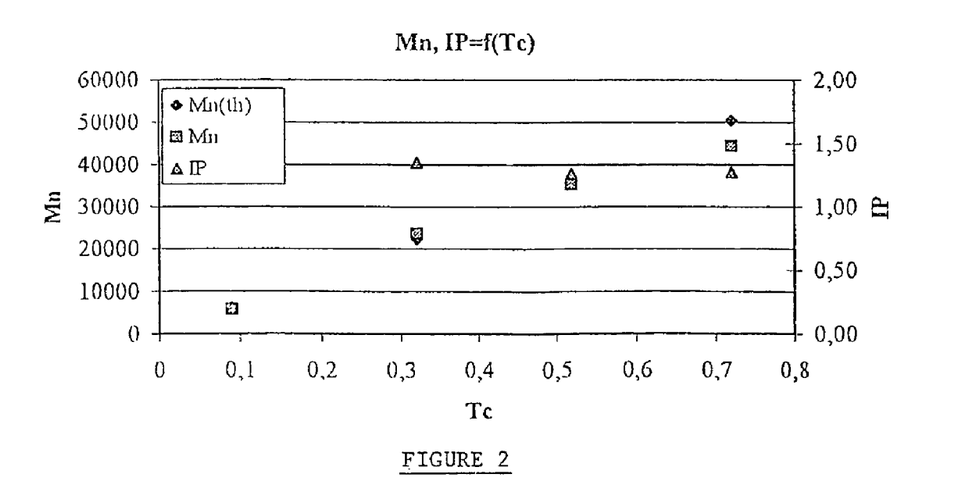
FIG. 2: Mn(th), Mn, PI=f(Dc)
Figure 3:
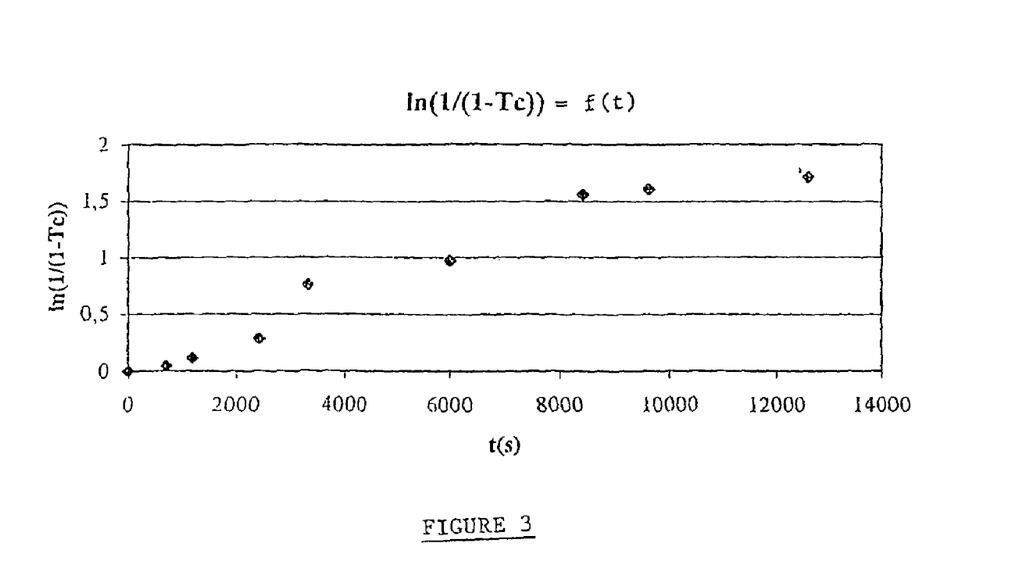
Figure 4:
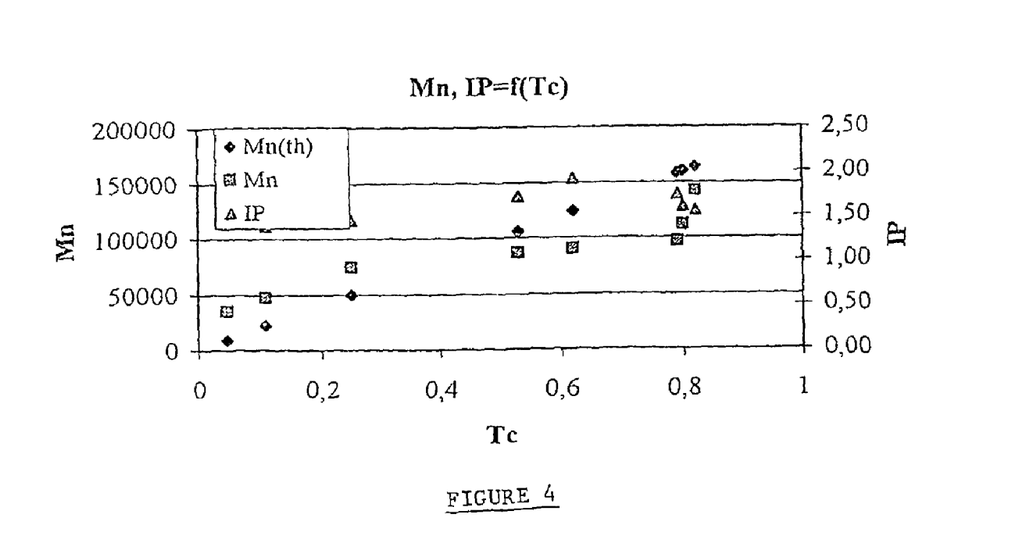

The kinetic results corresponding to the results of Example 3 are represented in the following figures:
FIG. 3: In(1/(1-Dc))=f(t);
FIG. 4: Mn(th), Mn, PI=f(Tc)

TABLE 3

Results of Example 4

| t (s) | Dc | In(1/(1 − Tc)) | Mn(th) | Mn | Mw | PI |
|---|---|---|---|---|---|---|
| 0 | 0 | 0 | | | | |
| 600 | 0.06 | 0.060 | 12 000 | 27 700 | 38 400 | 1.39 |
| 1 500 | 0.13 | 0.139 | 26 000 | 53 900 | 94 900 | 1.76 |
| 2 700 | 0.24 | 0.274 | 48 000 | 66 600 | 106 800 | 1.60 |
| 3 600 | 0.56 | 0.820 | 112 000 | 88 900 | 130 800 | 1.47 |
| 5 400 | 0.65 | 1.049 | 130 000 | 104 200 | 155 800 | 1.50 |
| 7 200 | 0.71 | 1.237 | 142 000 | 100 500 | 190 600 | 1.60 |
| 10 800 | 0.75 | 1.386 | 150 000 | 103 300 | 177 600 | 1.72 |
| 13 200 | 0.76 | 1.427 | 152 000 | 113 900 | 198 300 | 1.74 |
| 19 800 | 0.79 | 1.560 | 158 000 | 105 800 | 264 800 | 2.50 |

Figure 5:
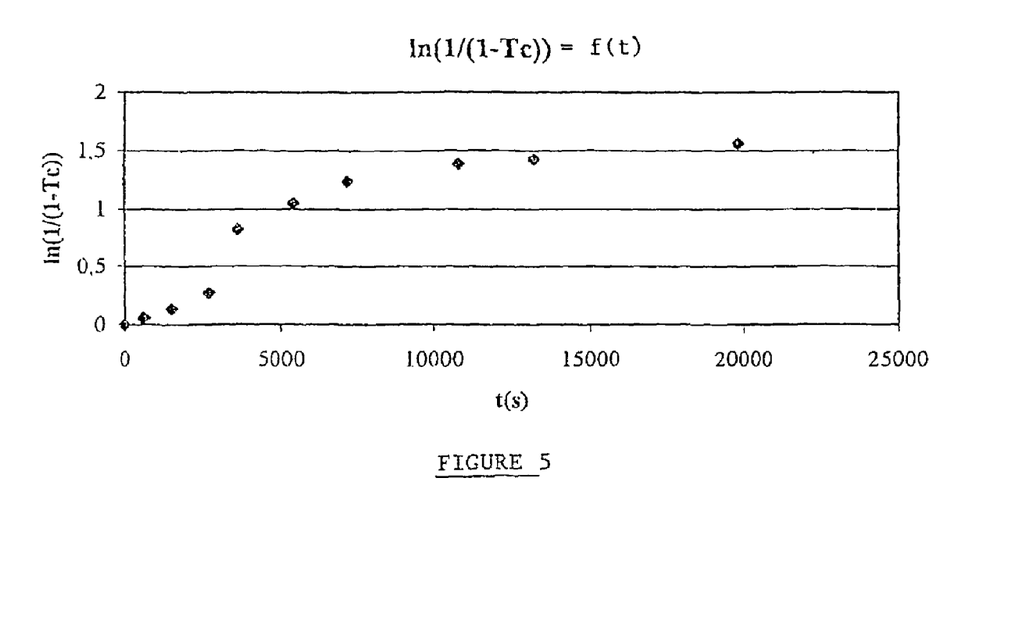
Figure 6:
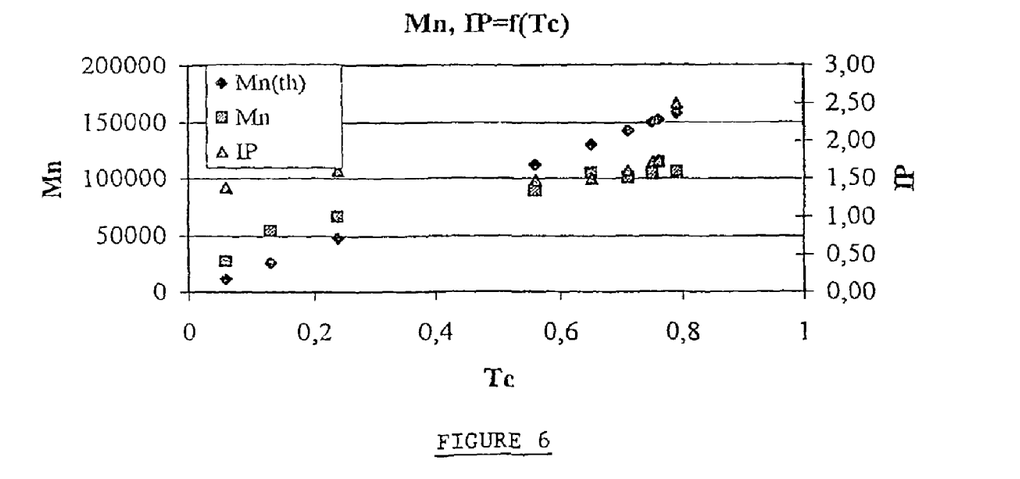

The kinetic curves corresponding to the results of Example 2 are represented in the following figures:
FIG. 5: In(1/(1-Dc))=f(t)
FIG. 6: Mn(th), Mn, PI=f(Tc)

The good alignment of the points on FIGS. 1, 2, 3 and 4 of the curves and the low polydispersity index (PI) are characteristics of a controlled radical polymerization of the butyl acrylate with the methylpropionic acid/SG1 alkoxyamine of the present invention.

EXAMPLE 5

Use of the methylpropionic acid/SG1 alkoxyamine as initiator in the copolymerization of methyl methacrylate (MMA) with butyl acrylate (BA)

Procedure:

The introduction was carried out of 0.953 g of methylpropionic acid/SG1 alkoxyamine, of 42.5 g of MMA and of 7.5 g of BA into a 100 ml glass reactor equipped with a reflux condenser, a jacket with circulation of oil, an inert gas (N$_2$) inlet and a temperature probe.

The medium was degassed by sparging with nitrogen for 20 minutes, then placed under mechanical stirring and brought to 95° C. Samples were withdrawn under an inert atmosphere at regular intervals.

Proton NMR allowed us to monitor the conversion of the monomer. The determination of the average molar masses of the polymer and of their polydispersity indices was carried out by SEC, using a universal calibration using poly(styrene) standards and the Mark-Houwink coefficients of poly(butyl acrylate) in THF.

The results are recorded in Table 4 below.
In this table:
Dc BA means degree of conversion of the butyl acrylate,
Dc M means degree of conversion of the methyl methacrylate,
Dc O means overall degree of conversion

TABLE 4

Results of Example 5

| t (s) | Dc BA | Dc M | Dc O | ln(1/1 − Dc BA) | ln(1/1 − Dc M) | ln(1/1 − Dc O) | Mn | PI |
|---|---|---|---|---|---|---|---|---|
| 900 | 0.11 | 0.23 | 0.22 | 0.11 | 0.27 | 0.24 | 10 400 | 1.47 |
| 2 100 | 0.15 | 0.32 | 0.30 | 0.16 | 0.38 | 0.35 | 13 500 | 1.37 |
| 3 300 | 0.17 | 0.38 | 0.35 | 0.19 | 0.48 | 0.43 | 14 700 | 1.41 |
| 5 700 | 0.25 | 0.48 | 0.45 | 0.28 | 0.66 | 0.60 | 16 200 | 1.38 |
| 9 000 | 0.30 | 0.74 | 0.67 | 0.35 | 1.35 | 1.12 | 17 800 | 1.37 |

Figure 7:
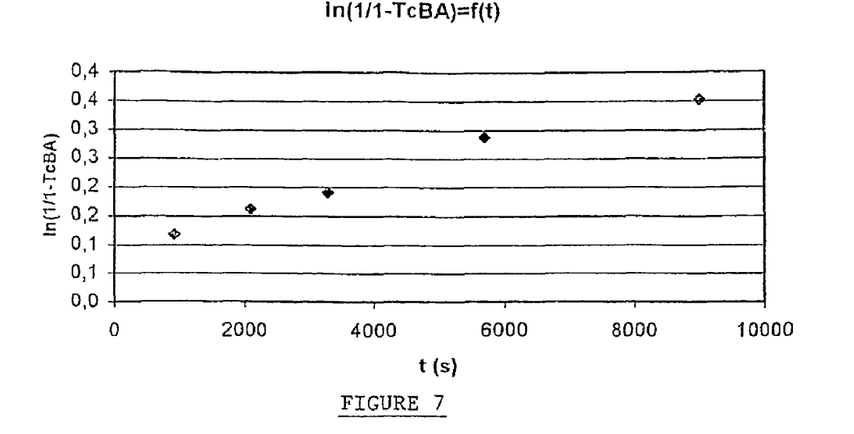
Figure 8:
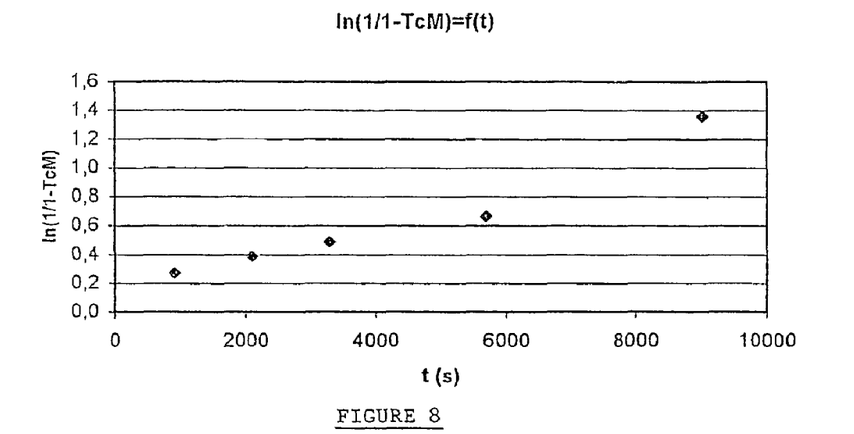
Figure 9:
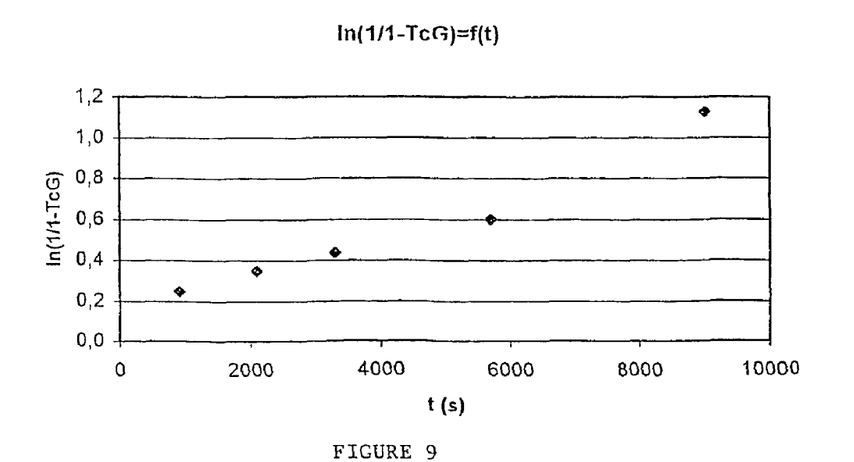
Figure 10:
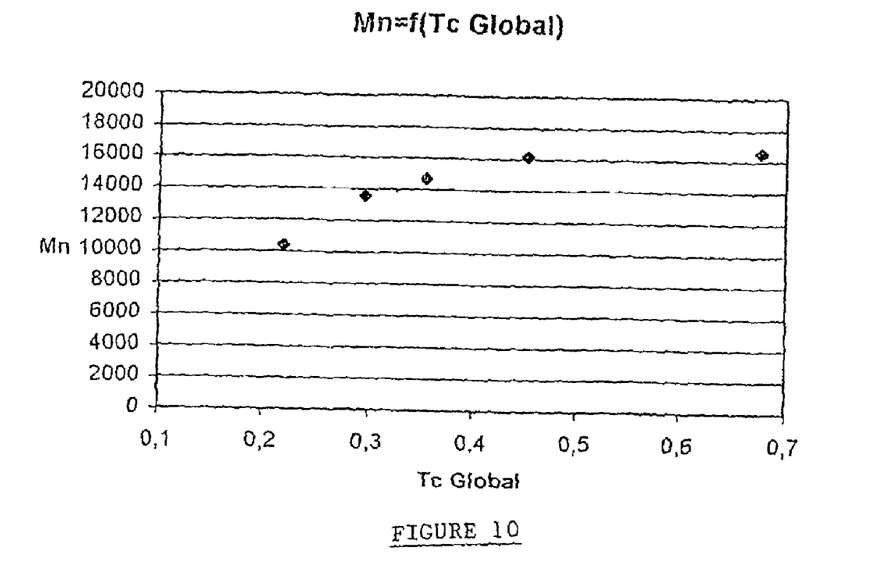
Figure 11:
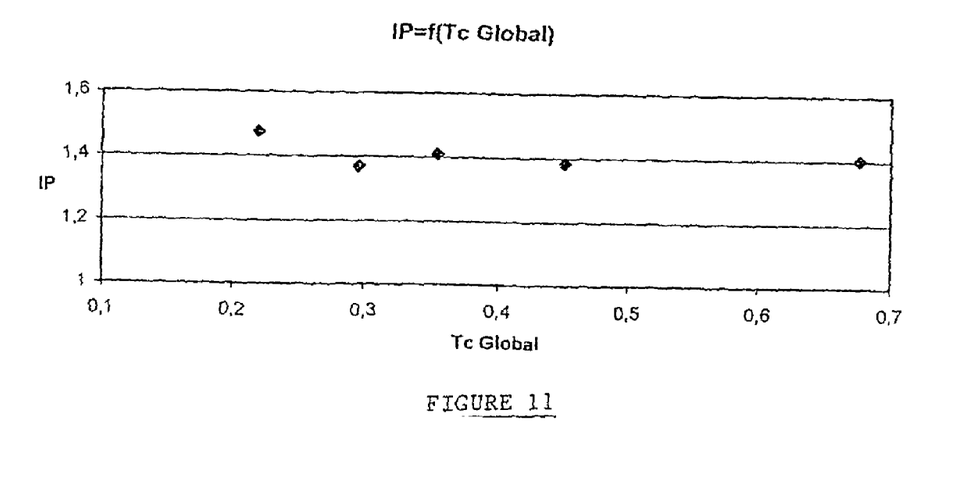

The results carried in Table 4 make it possible to plot the kinetic curves which are represented in the following figures:
FIG. 7: ln(1/1-Dc BA)=f(t);
FIG. 8: ln(1/1-Dc M)=f(t);
FIG. 9: ln(1/1-Dc O)=f(t);
FIG. 10: Mn=f(Dc O);
FIG. 11: PI=f(Dc O).

EXAMPLE 6

The operation is carried out as in Example 5, except that the copolymerization is carried out at 120° C. (instead of 95° C.) and that 0.0368 g of nitroxide SG1 is added.
The results are recorded in Table 5 below.

TABLE 5

Results of Example 6

| t (s) | Dc BA | Dc M | Dc O | ln(1/1 − Dc BA) | ln(1/1 − Dc M) | ln(1/1 − Dc O) | Mn | PI |
|---|---|---|---|---|---|---|---|---|
| 900 | 0.11 | 0.18 | 0.17 | 0.12 | 0.20 | 0.24 | 19 700 | 1.15 |
| 2 100 | 0.05 | 0.27 | 0.24 | 0.05 | 0.32 | 0.35 | 26 300 | 1.23 |
| 3 300 | 0.17 | 0.31 | 0.29 | 0.19 | 0.37 | 0.43 | 37 500 | 1.20 |
| 4 500 | 0.13 | 0.33 | 0.30 | 0.14 | 0.41 | 0.60 | 46 400 | 1.23 |
| 8 100 | 0.15 | 0.48 | 0.43 | 0.16 | 0.65 | 1.12 | 61 600 | 1.22 |
| 10 200 | 0.26 | 0.62 | 0.56 | 0.31 | 0.97 | 1.12 | 71 300 | 1.24 |

Figure 12:
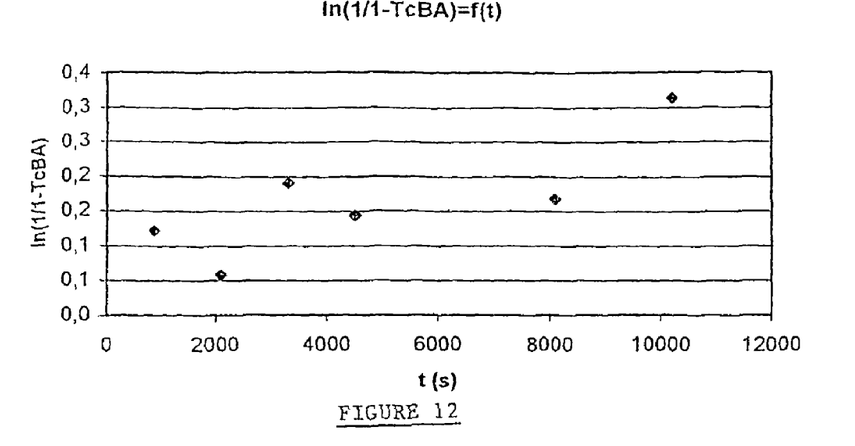
Figure 13:
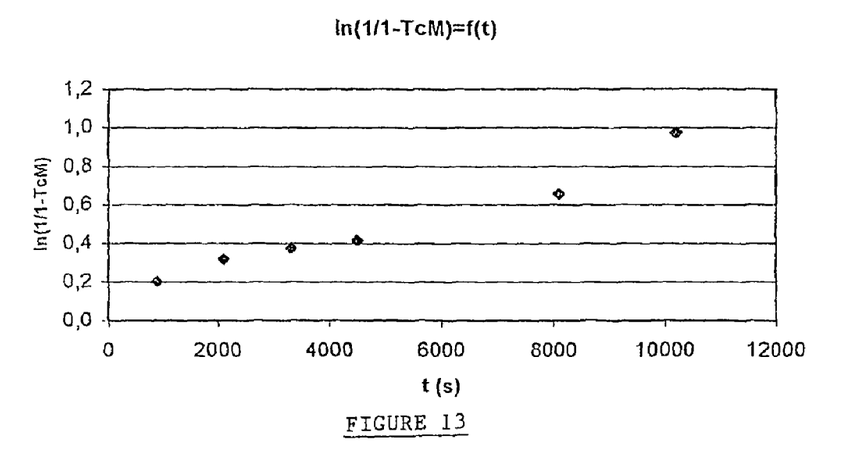
Figure 14:
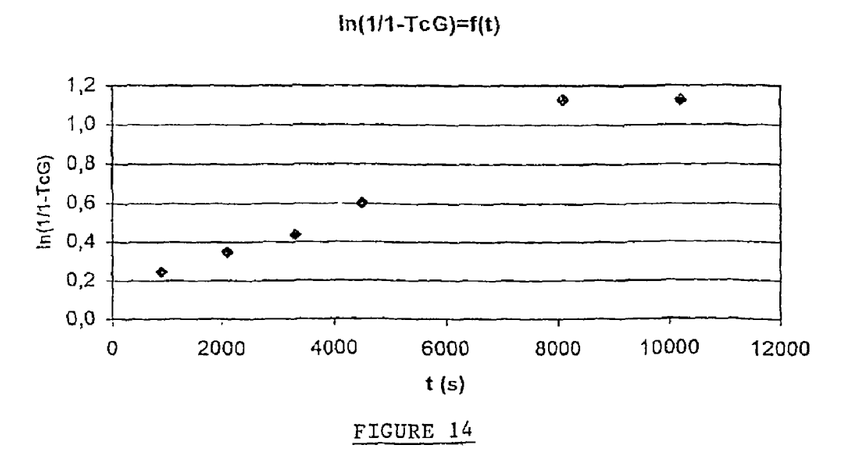
Figure 15:
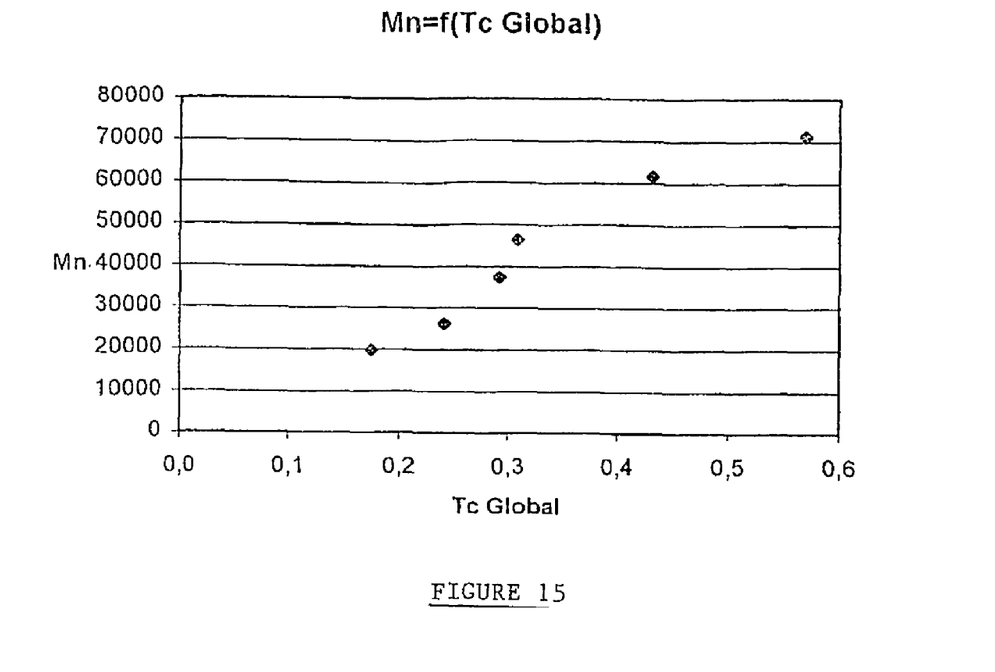
Figure 16:
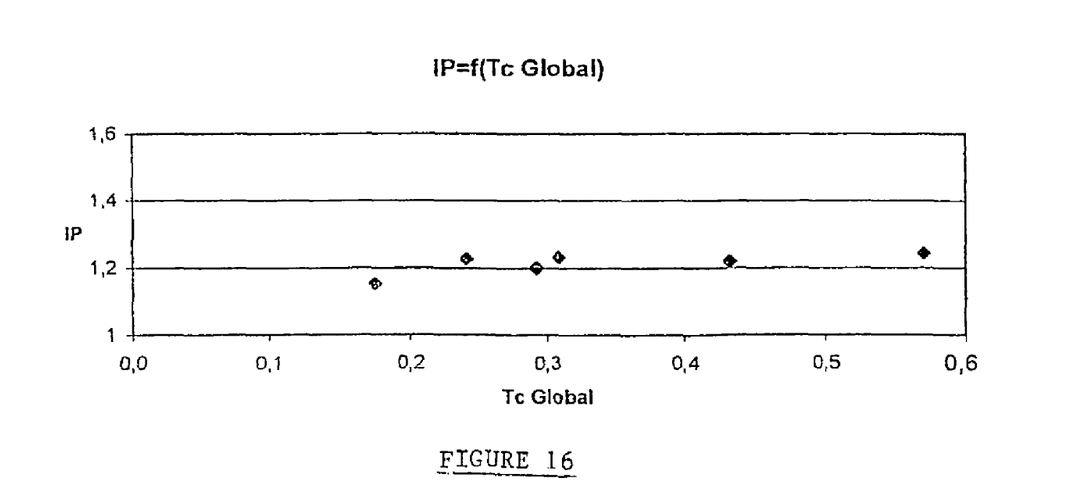

The results carried in Table 5 make it possible to plot the kinetic curves which are represented in the following figures:
FIG. 12: ln(1/1-Dc BA)=f(t);
FIG. 13: ln(1/1-Dc M)=f(t);
FIG. 14: ln(1/1-Dc O)=f(t);
FIG. 15: Mn=f(Dc Overall);
FIG. 16: PI=f(Dc Overall).

EXAMPLES 7 et 8

Use of the methylpropionic acid/SG1 alkoxyamine as initiator in the polymerization of methyl methacrylate (MMA)
Procedure:
10 g of MMA and 198 g of methylpropionic acid/SG1 alkoxyamine are mixed in a 25 ml two-necked round-bottomed glass flask. The mixture is placed under a nitrogen atmosphere by carrying out 3 reduced pressure/nitrogen cycles, stirred (magnetic stirring) and subsequently brought to a predetermined polymerization temperature.

EXAMPLE 7

Polymerization temperature: 25° C.
The results are recorded in Table 6 below.
In this table, Dc M means degree of conversion of the methyl methacrylate.

TABLE 6

Results of Example 7

| Time (hours) | Dc M | Mn | PI |
|---|---|---|---|
| 2 | 0.13 | 11 800 | 1.9 |
| 4 | 0.14 | 12 900 | 1.8 |
| 21 | 0.16 | 14 800 | 1.7 |
| 29 | 0.18 | 17 500 | 1.6 |
| 45 | 0.20 | 19 600 | 1.5 |
| 69 | 0.22 | 20 700 | 1.4 |

EXAMPLE 8

Polymerization temperature: 45° C.
The results are recorded in Table 7 below.
In this table, Dc M means degree of conversion of the methyl methacrylate.

TABLE 7

Results of Example 8

| Time (minutes) | Dc M |
|---|---|
| 15 | 0.24 |
| 30 | 0.34 |
| 45 | 0.39 |
| 90 | 0.55 |
| 135 | 0.68 |

EXAMPLE 9

Polymerization of styrene in the presence of the methylpropionic acid/SG1 alkoxyamine according to the present invention 30 g of styrene (0.288 mol) and 1.143 g of methylpropionic acid/SG1 (3 mmol) are placed in a three-necked flask equipped with a reflux condenser and a magnetic stirrer. The solution is degassed by sparging with nitrogen for 20 minutes. The reaction mixture is heated to 123° C. The progress of the polymerization is monitored by $^1$H NMR on samples withdrawn every 30 minutes. At the end of the reaction (the duration of polymerization is 5 h 30), the polymer is dissolved in THF and then precipitated from pentane.

The polymer is recovered by filtering the solution and then dried on a vacuum line. 24 g (yield: 90%) of a polymer P1 are obtained, which polymer has the structure:

P1 with a molecular mass $\overline{Mn}$ approximately equal to 10 000.

EXAMPLE 10

Synthesis of a polymer P2 with the structure:

P2

5 g of polymer P1 obtained above in Example 9 (0.45 mmol) and CH$_2$Cl$_2$ are introduced into a two-necked flask equipped with a stirring system and a septum. The solution is degassed by sparging with nitrogen for 10 minutes.

0.34 ml of SOCl$_2$ (4.8 mmol) is introduced through the septum using a syringe.

The mixture is stirred at ambient temperature under an inert atmosphere for 2 hours.

The solution is subsequently concentrated on a reduced pressure line (pressure of $10^{-1}$ mbar) to evaporate the CH$_2$Cl$_2$ and excess SOCl$_2$.

The two-necked flask is placed under nitrogen and then THF, capable of dissolving the polymer SG1[CH(C$_6$H$_5$)—CH$_2$]$_n$C(CH$_3$)$_2$C(O)Cl, is added thereto, followed by a solution comprising 0.13 ml of triethylamine and 0.122 g of 4-dimethylaminopyridine (DMAP) (1 mmol) and then 0.34 ml of CF$_3$CH$_2$OH (4.80 mmol) in THF.

The immediate appearance of a white precipitate is noticed. The reaction medium is stirred for approximately 2 hours at ambient temperature. The precipitate is removed by filtration and then the filtrate is evaporated under reduced pressure.

The polymer P2 obtained is purified by dissolving in THF and then reprecipitated from pentane. The product is subsequently filtered off and dried on a reduced pressure line. 5.01 g of P2 are obtained.

Analytical Characteristics:

$^{19}$F NMR (CDCl$_3$, 282.4 MHz): δ=74.02 ppm
$^{31}$P NMR (CDCl$_3$, 121.49 MHz):
δ=25.61 ppm (singlet) (1 dia. 67%)
δ=24.43 ppm (singlet) (1 dia. 33%)

EXAMPLE 11

Synthesis of a polymer P3 with the structure:

P3

The operation is carried out as in Example 10 above, except that 0.5 equivalent of ethanediol is used instead of 4.80 mmol of CF$_3$CH$_2$OH and that, in the first stage (formation of the acid chloride), the reaction medium is brought to 40° C. for 2 h and that, in the following stage [coupling stage], the reaction medium is brought to ambient temperature for 16 h.

The degree of coupling, determined by GPC, is 47%.

EXAMPLE 12

Synthesis of a polymer P4 with the structure:

P4 by coupling between the polymer P1 and a PEO-OMe block ($\overline{Mn}$=750 g.mol$^{-1}$)

Procedure:

P1, dissolved in THF, is placed in a two-necked flask equipped with a stirring system and a septum. The solution is degassed by sparging with nitrogen for 10 minutes. Thionyl chloride (10 equivalents) is introduced through the septum using a syringe. The mixture is stirred under an inert atmosphere for 4 hours at 40° C. The solution is subsequently concentrated on a reduced pressure line to evaporate the solvent and the excess thionyl chloride.

A solution of triethylamine (1 equivalent), of 4-dimethylaminopyridine (DMAP) (catalytic) and of the PEO-OMe block (3 equivalents) in DMF is then added to the two-necked flask placed under nitrogen. The mixture is stirred for 17 hours at 80° C.

P4 and P1 are separated from the excess PEO-OMe by selective precipitation from ethanol, filtered off and then dried on a vacuum line. The degree of coupling, determined by proton NMR, is 7%.

EXAMPLE 13

Synthesis of the polymer P4 using dicyclohexylcarbodiimide (DCC) instead of triethylamine without passing through the acid chloride stage Procedure:

P1 (1 equivalent), α-methoxylated-poly(ethylene oxide) (1 equivalent) and 4-dimethylaminopyridine (DMAP) (0.8 equivalent) are placed in anhydrous dichloromethane in a round-bottomed flask equipped with a magnetic stirrer and a reflux condenser. The solution is degassed by sparging with nitrogen for 10 to 15 minutes. Dicyclohexylcarbodiimide

(DCC) (2.6 equivalents), dissolved in the minimum amount of $CH_2Cl_2$, is added to the mixture using a syringe.

The mixture is left to stir at ambient temperature for 24 hours.

Subsequently, P4 and P1 are separated from the excess PEO-OMe by selective precipitation from ethanol, filtered off and then dried on a vacuum line. The degree of coupling, determined by proton NMR, is 38%.

The invention claimed is:

1. Alkoxyamines of the formula: Sodium 2-methyl-2-[N-(tert-butyl)-N-(diethoxyphosphoryl-2,2-dimethylpropyl) aminoxy]propionate:

2. A method for (co)polymerizations of at least one monomer which can be polymerized by the radical route under bulk, solution, emulsion, suspension or miniemulsion conditions comprising reacting, with said at least one monomer, in the absence of free nitroxide, alkoxyamines of formula:

in which R represents a linear or branched alkyl radical having a number of carbon atoms ranging from 1 to 3, $R^1$ represents a hydrogen atom or a residue:

in which $R^3$ represents a linear or branched alkyl radical having a number of carbon atoms ranging from 1 to 20, and $R^2$ represents a phenyl radical, an alkali metal, $H_4N^+$, $Bu_4N^+$ or $Bu_3HN^+$, exhibiting a kinetic dissociation constant kd, measured at 120° C. by EPR, of greater than $0.05\ s^{-1}$ and preferably of greater than $0.1\ s^{-1}$.

3. The method of claim 2 wherein $R=CH_3$—, $R^1=H$ and $R^2$ is selected from the group consisting of Li and Na.

4. The method of claim 2 wherein said an alkali metal is selected from the group consisting of Li, Na and K.

5. The method of claim 2, characterized in that the monomer or monomers which can be polymerized by the radical route are chosen from vinylaromatic monomers, dienes, (meth)acrylic monomer, (meth)acrylate monomers, methyl acrylate, ethyl acrylate, butyl acrylate, ethylhexyl acrylate, phenyl acrylate, 2-hydroxyethyl acrylate, 2-methoxyethyl acrylate, methoxypolyethylene glycol acrylates, ethoxypolyethylene glycol acrylates, methoxypolypropylene glycol acrylates, methoxypolyethylene glycol-polypropylene glycol acrylates or their mixtures, 2-(dimethylamino)ethyl acrylate (ADAME), [2-(acryloyloxy)ethyl]-trimethylammonium chloride, [2-(acryloyloxy)ethyl]trimethylammonium sulphate, [2-(acryloyloxy)ethyl]dimethylbenzylammonium chloride, [2-(acryloyloxy)ethyl]dimethyl-benzylammonium sulphate, methacrylic acid or its salts, methyl methacrylate, lauryl methacrylate, cyclohexyl methacrylate, allyl methacrylate, phenyl methacrylate, 2-hydroxyethyl methacrylate, 2-hydroxypropyl methacrylate, 2-ethoxyethyl methacrylate, methoxypolyethylene glycol methacrylates, ethoxypolyethylene glycol methacrylates, methoxypolypropylene glycol methacrylates, methoxypolyethylene glycol-polypropylene glycol methacrylates, 2-(dimethylamino)ethyl methacrylate (MADAME), [2-(methacryloyloxy)ethyl]trimethylammonium chloride, [2-(methacryloyloxy)ethyl]trimethylammonium sulphate, [2-(methacryloyloxy)ethyl]dimethylbenzylammonium chloride, [2-(methacryloyloxy)ethyl] dimethylbenzylammonium sulphate, 2,2,2-trifluoroethyl methacrylate, 3-methacryloyloxypropyltrimethylsilane, ethylene glycol methacrylate phosphate, hydroxyethylimidazolidone methacrylate, hydroxyethylimidazolidinone methacrylate, 2-(2-oxo-1-imidazolidinyl)ethyl methacrylate, acrylonitrile, substituted (meth)acrylamides, 4-acryoylmorpholine, N-methylolacrylamide, acrylamidopropyltrimethylammonium chloride (APTAC), acrylamidomethylpropanesulphonic acid (AMPS) or is salts, methacrylamide, N-methylolmethacrylamide, methacrylamidopropyltrimethylammonium chloride (MAPTAC), itaconic acid, maleic acid or its salts, maleic anhydride, vinylpyridine, vinylpyrrolidinone, (alkoxy)poly(alkylene glycol) vinyl ethers, vinylpyrrolidinone, (alkoxy)poly(alkylene glycol) divinyl ethersor a mixture of at least two of said monomers.

6. The method according to claim 5, characterized in that at least one of the monomers is butyl acrylate.

7. The method according to claim 5, characterized in that at least one of the monomers is methyl methacrylate.

8. The method according to claim 5, characterized in that the monomers comprise a mixture of butyl acrylate and of methyl methacrylate.

* * * * *